United States Patent [19]

Uchiyama et al.

[11] Patent Number: 5,436,364
[45] Date of Patent: Jul. 25, 1995

[54] PROCESS FOR PRODUCING DIMETHYL 2,6-NAPHTHALENE-DICARBOXYLATE

[75] Inventors: Seiji Uchiyama; Hiroshi Machida; Rieko Nakano; Ryuji Hasemi, all of Niigata, Japan

[73] Assignee: Mitsubishi Gas Chemical Company, Inc., Tokyo, Japan

[21] Appl. No.: 263,466

[22] Filed: Jun. 22, 1994

[30] Foreign Application Priority Data

Sep. 2, 1993 [JP] Japan .................................. 5-218607

[51] Int. Cl.$^6$ .............................................. C07C 69/76
[52] U.S. Cl. ...................................................... 560/80
[58] Field of Search ............................................ 560/80

[56] References Cited

U.S. PATENT DOCUMENTS 5,262,560  11/1993  Holzhauer et al. .................... 560/78

FOREIGN PATENT DOCUMENTS 2455666  6/1975  Germany .
1437897  6/1976  United Kingdom .

OTHER PUBLICATIONS

Database WPI, Week 9347, Derwent Publications Ltd., London, GB; AN 93-374653 of JP-A-5 279 462 (Teijin Ltd), Oct. 1993.

Primary Examiner—José G. Dees
Assistant Examiner—Samuel Barts
Attorney, Agent, or Firm—Frishauf, Holtz, Goodman & Woodward

[57] ABSTRACT

A process for producing dimethyl 2,6-naphthalene-dicarboxylate by reacting 2,6-naphthalene-dicarboxylic acid with methanol which comprises effecting the reaction at 200° to 350° C. in the presence of trimethyl trimellitate as an essential solvent and optionally, at least one solvent selected from methyl benzoate, methyl toluate and dimethyl o-phthalate preferably by at least two-stage continuous reaction method. The above process is capable of enhancing the rate of esterification reaction and producing purified objective product in high yield for a long period of time in a stable operation without causing any operational trouble such as corrosion and clogging the production equipment.

23 Claims, No Drawings

PROCESS FOR PRODUCING DIMETHYL 2,6-NAPHTHALENE-DICARBOXYLATE

BACKGROUND OF THE INVENTION

1. Field of the Invention

The present invention relates to a process for producing dimethyl 2,6-naphthalene-dicarboxylate which is useful as a starting raw material for highly functional polyester.

2. Description of the Related Arts

As a process for producing dimethyl 2,6-naphthalene-dicarboxylate through the esterification of 2,6-naphthalene-dicarboxylic acid by the use of methanol, there have heretofore been known a process by using a mineral acid such as sulfuric acid as a catalyst (Japanese Patent Publication No. 174/1974), a process by using an oxide or a salt of any of various metals as a catalyst (Japanese Patent Application Laid-Open Nos. 83360/1975, 83361/1975, 8252/1976 and 48641/1976), a noncatalytic process in which the reaction is carried out at a temperature not lower than the critical temperature of methanol (Japanese Patent Application Laid-Open No. 95253/1975), a continuous esterification process (Japanese Patent Application Laid-Open Nos. 96574/1973 and Japanese Patent Publication No. 36179/1981), a process by using dimethyl phthalate as a solvent (Japanese Patent Application Laid-Open No. 200657/1990) and the like.

The above-mentioned processes are proposed as the methods of accelerating the reaction, since the rate of the esterification reaction is extremely low because of 2,6-naphthalene-dicarboxylic acid being sparingly soluble in methanol.

However, most of the above-mentioned processes are not necessarily satisfactory from the industrial viewpoint such as equipment and operation and is accompanied with various problems to be solved.

For example, the process by using a mineral acid such as sulfuric acid suffers the disadvantages that the equipment cost is undesirably increased by the necessity for corrosion resistance of the reactor and that a considerable amount of methanol is lost owing to the by-production of dimethyl ether accompanying the esterification reaction. In addition, the process by using a metallic compound as a catalyst, the noncatalytic process in which the reaction is carried out at a temperature not lower than the critical temperature of methanol and the like process are still unsatisfactory from the industrial viewpoint such as the rate of reaction.

Moreover, the continuous esterification process involves the problems that the sparingly methanol-soluble 2,6-naphthalene-dicarboxylic acid necessitates handling it as a solid, and clogging or the like is caused in the production equipment or piping because of the high melting point of dimethyl 2,6-naphthalene-dicarboxylate that is the esterified product, whereby special equipment and methods are made necessary in order to operate the production equipment in a stable manner.

Further, the process by using dimethyl phthalate as a solvent involves such problems as the corrosion resistance of the reactor and the by-production of dimethyl ether as mentioned above due to the use of sulfuric acid as a catalyst.

SUMMARY OF THE INVENTION

In view of the foregoing, it is eagerly desired to develop an industrial process for producing dimethyl 2,6-naphthalene-dicarboxylate capable of enhancing the rate of the esterification reaction, eliminating the problem with production equipment such as corrosion and at the same time, overcoming the clogging trouble inside the equipment in the case of continuous process.

As a countermeasure against the above-described problems, a process by using a reactive solvent is taken into consideration. The requirements for such a reactive solvent include high solubilities for not only 2,6-naphthalene-dicarboxylic acid and methanol but also dimethyl 2,6-naphthalene-dicarboxylate as the objective product, fluidity of the reaction mixture to be sufficiently maintained and the ease of its separation from the reaction products.

Under such circumstances, intensive research and investigation were accumulated by the present inventors in order to develop an industrial process for advantageously producing dimethyl 2,6-naphthalene-dicarboxylate with minimized amounts of unfavorable by-products by developing a variety of reactive solvents meeting the above-mentioned requirements. As a result, it has been found that by using, as a reactive solvent, trimethyl trimellitate that is in the form of liquid at ordinary temperature, it is made possible to accelerate the rate of esterification reaction, eliminate the clogging trouble inside the production equipment in the case of continuous process, and thereby carry out stable operation of the equipment. The present invention has been accomplished by the aforesaid finding.

Specifically the present invention provides a process for producing dimethyl 2,6-naphthalene-dicarboxylate which comprises reacting 2,6-naphthalene-dicarboxylic acid with methanol in the presence of trimethyl trimellitate as a solvent.

DESCRIPTION OF PREFERRED EMBODIMENT

There is no specific limitation to the process for producing the 2,6-naphthalene-dicarboxylic acid to be employed as the starting raw material in the present invention. There is usable, for example, the 2,6-naphthalene-dicarboxylic acid which is obtained by the oxidation of a 2-acyl-6-alkylnaphthalene or 2,6-dimethylnaphthalene.

Trimethyl trimellitate to be employed as a solvent in the present invention is in the form of liquid at ordinary temperature and exhibits the highest effect when used alone, but may be employed as a mixed solvent with at least one solvent selected from methyl benzoate, methyl toluate and dimethyl o-phthalate.

The amount of trimethyl trimellitate to be used in the process according to the present invention is 0.5 to 10, preferably 1.5 to 7 parts by weight based on one part by weight of 2,6-naphthalene-dicarboxylic acid. An amount thereof more than 10 parts by weight can advance esterification reaction but is economically disadvantageous taking into consideration the separation from the reaction product. On the other hand, an amount thereof less than 0.5 part by weight is unfavorable, since such an amount is not sufficient for accelerating the rate of esterification and improving the fluidity of the reaction products. In the case where mixed solvent is used, there is usable by mixing, any of the above-mentioned esters in an arbitrary amount but less than one part by weight based on one part by weight of trimethyl trimellitate.

The esterification temperature in the process according to the present invention is the range of preferably 200° to 350° C., more preferably 230° to 300° C. An esterification temperature lower than 200° C. unfavorable leads to a low rate of esterification, whereas that higher than 350° C. undesirably results in increased amounts of byproducts such as a polymer, dimethyl ether and the like, thereby lowering the yield of the objective product.

In the process according to the present invention, there is no need in particular, to use a catlyst.

However, in the case of using a catalyst, there is usable a catalyst other than a mineral acid such as sulfuric acid, which catalyst is exemplified by a titanic acid ester, molybdophosphoric acid, molybdenum oxide, beryllium sulfate, bismuth sulfate and the like.

The reaction method may be either batchwise or continuous, but continuous method is preferable from the industrial standpoint in which importance is attached to the elimination of clogging trouble inside the production equipment and to the implementation of smooth stable esterification reaction.

The process according to the present invention is put into practice preferably by at least two-stage reaction comprising the steps of feeding into a reactor, a slurry containing 2,6-naphthalene-dicarboxylic acid, methanol and trimethyl trimellitate and, when necessary, a catalyst to proceed with esterification reaction continuously, while withdrawing the product water and part of the unreacted methanol; and subsequently feeding into another reactor, the resultant esterified product along with fresh methanol to complete esterification reaction.

An example of esterification reaction according to the process of the present invention is described as follows.

A slurry containing 2,6-naphthalene-dicarboxylic acid and methanol each as a starting raw material, trimethyl trimellitate as a solvent and a catalyst is fed into an agitation type reactor to continuously proceed with esterification reaction by heating under pressure, while withdrawing the product water and part of the unreacted methanol. In the above-mentioned reaction, dimethyl 2,6-naphthalene-dicarboxylate is obtained in a yield of 90% or more. Thereafter, the resultant esterified product along with fresh methanol are fed into another reactor to complete the reaction, thereby attaining high yield of the objective product. The aforestated process enables continuous long-term stable esterification without causing any trouble of clogging inside the reaction equipment such as the reactors and piping. Then, the esterified product is distilled in a distillation column, where the trimethyl trimellitate is recovered from the top thereof enabling itself to be recycled as such through the reaction system, while dimethyl 2,6-naphthalene-dicarboxylate as the crude product is obtained from the bottom thereof. The crude product can be made into the objective purified dimethyl 2,6-naphthalene-dicarboxylate having a purity of at least 99.9% by further purifying steps such as distillation and crystallization.

According to the process of the present invention, it is made possible to enhance the rate of reaction as compared with conventional processes, continuously feed 2,6-naphthalene-dicarboxylic acid in the form of solid into a reactor without causing any trouble of clogging, smoothly withdraw the resultant esterified product and thereby continuously produce the objective purified dimethyl 2,6-naphthalene-dicarboxylate in high yield for a long period of time in a stable operation, thus rendering the present invention highly significant from the industrial point of view.

In the following, the present invention will be described in more detail with reference to comparative examples and examples, which however shall not be construed to limit the present invention thereto.

EXAMPLE 1

Into a 100 ml reactor made of stainless steel type 316 were fed 6.0 g of 2,6-naphthalene-dicarboxylic acid, 36.0 g of methanol and 20.0 g of trimethyl trimellitate as a solvent, and the reaction was put into practice under shaking in an oil bath at a temperature of 270° C. for 20 min. Then, the reactor was allowed to cool and thereafter the content in the reactor was taken out therefrom in dimethylformamide to dissolve thereinto. The results of analysis for the reaction product by gas chromatography indicated 94.5 mol % yield of dimethyl 2,6-naphthalene-dicarboxylate based on 2,6-naphthalene-dicarboxylic acid; 99.5% efficiency of equilibrium achievement; and at most 0.5 mol % by-produced dimethyl ether based on methanol that was fed into the reactor.

EXAMPLE 2

The procedure in Example 1 was repeated to carry out esterification except that the reaction was put into practice at 280° C. (instead of 270° C.) for 15 min. (instead of 20 min). The results of analysis for the reaction product indicated 94.5 mol % yield of the objective dimethyl 2,6-naphthalene-dicarboxylate based on 2,6-naphthalene-dicarboxylic acid; 99.5% efficiency of equilibrium achievement; and at most 0.5 mol % by-produced dimethyl ether based on methanol that was fed into the reaction system.

EXAMPLE 3

The procedure in Example 1 was repeated to carry out esterification except that 12.0 g of trimethyl trimellitate was fed into the reaction. The results of analysis for the reaction product indicated 94.2 mol % yield of the objective dimethyl 2,6-naphthalene-dicarboxylate based on 2,6-naphthalene-dicarboxylic acid; 99.1% efficiency of equilibrium achievement; and at most 1.0 mol % by-produced dimethyl ether based on methanol that was fed into the reaction system.

EXAMPLE 4

The procedure in Example 1 was repeated to carry out esterification except that mixed solvent containing 10.0 g of trimethyl trimellitate and 2.0 g of dimethyl o-phthalate was fed into the reactor. The results of analysis for the reaction product indicated 92.7 mol % yield of the objective dimethyl 2,6-naphthalene-dicarboxylate based on 2,6-naphthalene-dicarboxylic acid; 97.6% efficiency of equilibrium achievement; and at most 1.2 mol % by-produced dimethyl ether based on methanol that was fed into the reaction system.

EXAMPLE 5

The procedure in Example 1 was repeated to carry out esterification except that mixed solvent containing 10.0 g of trimethyl trimellitate and 2.0 g of methyl m-toluate was fed into the reactor. The results of analysis for the reaction product indicated 91.8 mol % yield of the objective dimethyl 2,6-naphthalene-dicarboxylate based on 2,6-naphthalene-dicarboxylic acid; 96.6% efficiency of equilibrium achievement; and at most 1.0 mol % by-produced dimethyl ether based on methanol that was fed into the reaction system.

EXAMPLE 6

The procedure in Example 1 was repeated to carry out esterification except that mixed solvent containing 10.0 g of trimethyl trimellitate and 2.0 g of methyl benzoate was fed into the reactor. The results of analysis for the reaction product indicated 91.2 mol % yield of the objective dimethyl 2,6-naphthalene-dicarboxylate based on 2,6-naphthalene-dicarboxylic acid; 96.0% efficiency of equilibrium achievement; and at most 1.0 mol % by-produced dimethyl ether based on methanol that was fed into the reaction system.

COMPARATIVE EXAMPLE 1

The procedure in Example 1 was repeated to carry out esterification except that no solvent was fed into the reactor. The results of analysis for the reaction product indicated 58.5 mol % yield of the objective dimethyl 2,6-naphthalene-dicarboxylate based on 2,6-naphthalene-dicarboxylic acid; 61.5% efficiency of equilibrium achievement; and 1.5 mol % by-produced dimethyl ether based on methanol that was fed into the reaction system.

COMPARATIVE EXAMPLE 2

The procedure in Example 2 was repeated to carry out esterification except that no solvent was fed into the reactor. The results of analysis for the reaction product indicated 81.5 mol % yield of the objective dimethyl 2,6-naphthalene-dicarboxylate based on 2,6-naphthalene-dicarboxylic acid; 85.8% efficiency of equilibrium achievement; and 1.5 mol % by-produced dimethyl ether based on methanol that was fed into the reaction system.

COMPARATIVE EXAMPLE 3

Into a 200 ml reactor lined inside with Teflon were fed 12.0 g of 2,6-naphthalene-dicarboxylic acid, 72.0 g of methanol, 20.0 g of dimethyl o-phthalate as a solvent and sulfuric acid as a catalyst in an amount of 10% by weight based on 2,6-naphthalene-dicarboxylic acid, and the reaction was put into practice at a temperature of 130° C. for 6 hours. The results of analysis for the reaction product indicated 94.5 mol % yield of the objective dimethyl 2,6-naphthalene-dicarboxylate based on 2,6-naphthalene-dicarboxylic acid; and by-produced dimethyl ether in an amount of as large as 8 mol % based on methanol that was fed into the reaction system.

EXAMPLE 7

A slurry was prepared from 2,6-naphthalene-dicarboxylic acid, trimethyl trimellitate and methanol in a ratio by weight of 1:3:3 and further incorporated with molybdenum oxide as a catalyst in an amount of 0.1% by weight based on 2,6-naphthalene-dicarboxylic acid. The resultant mixture as feed solution was fed in a 1,000 ml autoclave equipped with a stirrer at a feed rate of 959 g/hr to proceed with esterification reaction at a reaction temperature maintained at 270° C. under a reaction pressure maintained at 25 kg/cm$^2$G, while continuously withdrawing the product water and part of unreacted methanol from the gas phase and the esterified product from the liquid phase, respectively.

The residence time of the liquid phase in the reactor was 2 hours. After continuous 100 hours of reaction, the esterified product was analyzed. The results pointed out 91.5 mol % yield of dimethyl 2,6-naphthalene-dicarboxylate based on 2,6-naphthalene-dicarboxylic acid.

Subsequently, a feed solution in the form of slurry was prepared from one part by weight of the resultant esterified product and one part by weight of methanol and was fed in the same type of autoclave as used in preceding stage at a feed rate of 2030 g/hr to proceed with esterification reaction in the same manner as above at a reaction temperature maintained at 270° C. under a reaction pressure maintained at 25 kg/cm$^2$G. The residence time of the liquid phase in the reactor was one hours. After continuous 100 hours of reaction, the esterified product was analyzed. The results pointed out 99.3 mol % yield of the objective dimethyl 2,6-naphthalene-dicarboxylate based on 2,6-naphthalene-dicarboxylic acid which had originally been fed to the reaction system.

Throughout the above-mentioned operation, the process was free from any clogging due to solid, whereby stable operation was made possible to continue.

COMPARATIVE EXAMPLE 4

The procedure in Example 7 was repeated to carry continuous esterification except that trimethyl trimellitate was not incorporated in the feed solution. As a result, during the first-stage reaction, clogging was caused in the line for withdrawing the esterified product from the liquid phase after 10 hours from the start of the reaction. The vapor from heated methanol was blown into the clogged line to remove the clogging product, and then the reaction was continued for 50 hours, during which clogging was caused four times and the same removal procedure was carried out at every time of clogging. The results of analysis for the esterified product indicated 85.7 mol % yield of dimethyl 2,6-naphthalene-dicarboxylate based on 2,6-naphthalene-dicarboxylic acid which was fed to the reaction system.

Subsequently, the second-stage reaction was performed by feeding the mixture of the resultant esterified product and fresh methanol added thereto. As a result, as is the case with the first-stage reaction, clogging was brought about in the line for withdrawing the esterified product after 13 hours from the start of reaction. The clogging product was removed in the same manner, and the reaction was continued for further 52 hours, during which clogging was caused four times each followed by the same removal procedure. The results of analysis for the esterified product pointed out 95.3 mol % yield of the objective dimethyl 2,6-naphthalene-dicarboxylate based on 2,6-naphthalene-dicarboxylic acid which had originally been fed to the reaction system.

What is claimed is:

1. A process for producing dimethyl 2,6-naphthalene-dicarboxylate which comprises reacting 2,6-naphthalene-dicarboxylic acid with methanol in the presence of a solvent comprising trimethyl trimellitate.

2. The process according to claim 1 wherein the amount of trimethyl trimellitate is 0.5 to 10 parts by weight based on one part by weight of naphthalene-dicarboxylic acid.

3. The process according to claim 1 wherein the solvent comprises trimethyl trimellitate and at least one solvent selected from the group consisting of methyl benzoate, methyl toluate and dimethyl o-phthalate to form a mixed solvent.

4. The process according to claim 3 wherein the amount of at least one solvent selected from the group consisting of methyl benzoate, methyl toluate and dimethyl o-phthalate is at most one part by weight based on one part by weight of trimethyl trimellitate.

5. The process according to claim 1 wherein the reaction is carried out at a temperature of 200° to 350° C.

6. The process according to claim 1 where the reaction is carried out by a continuous reaction method.

7. The process according to claim 1 wherein the reaction is carried out in the presence of at least one catalyst selected from the group consisting of titanic acid ester, molybdophosphoric acid, molybdenum oxide, beryllium sulfate and bismuth sulfate.

8. A process for producing dimethyl 2,6-naphthalene-dicarboxylate which comprises the steps of feeding a slurry containing 2,6-naphthalene-dicarboxylic acid, methanol and trimethyl trimellitate in a reactor; continuously esterifying the 2,6-naphthalene-dicarboxylic acid with methanol while withdrawing product water and part of unreacted methanol; and feeding the resultant esterified product along with fresh methanol to another reactor to continue esterification.

9. The process according to claim 8 wherein the reaction is carried out in the presence of at least one catalyst selected from the group consisting of titanic acid ester, molybdophosphoric acid, molybdenum oxide, beryllium sulfate and bismuth sulfate.

10. The process according to claim 8 wherein
   the reaction is carried out at a temperature of 230° to 300° C.; and
   the amount of trimethyl trimellitate is 1.5 to 7 parts by weight based on one part by weight of naphthalene-dicarboxylic acid.

11. The process according to claim 10 wherein the solvent comprised trimethyl trimellitate and at least one solvent selected from the group consisting of methyl benzoate, methyl toluate and dimethyl o-phthalate to form a mixed solvent;
   the amount of said at least one solvent selected from the group consisting of methyl benzoate, methyl toluate and dimethyl o-phthalate is at most one part by weight based on one part by weight of trimethyl trimellitate; and
   the mixed solvent is 1.5 to 7 parts by weight based on one part by weight of naphthalene-dicarboxylic acid.

12. The process according to claim 10 wherein the reaction is carried out in the presence of at least one catalyst selected from the group consisting of titanic acid ester, molybdophosphoric acid, molybdenum oxide, beryllium sulfate and bismuth sulfate.

13. The process according to claim 11 wherein the reaction is carried out in the presence of at least one catalyst selected from the group consisting of titanic acid ester, molybdophosphoric acid, molybdenum oxide, beryllium sulfate and bismuth sulfate.

14. The process according to claim 8 wherein the reaction is carried out at a temperature of about 270° to 280° C. and wherein the amount of solvent is about 2 to 3⅓ parts by weight based on one part by weight of naphthalene-dicarboxylic acid.

15. The process according to claim 14 wherein the solvent comprises trimethyl trimellitate and at least one solvent selected from the group consisting of methyl benzoate, methyl toluate and dimethyl o-phthalate to form a mixed solvent.

16. The process according to claim 14 wherein the reaction is carried out in the presence of molybdenum oxide as a catalyst.

17. The process according to claim 1 wherein
   the reaction is carried out at a temperature of 230° to 300° C.;
   the amount of trimethyl trimellitate is 1.5 to 7 parts by weight based on one part by weight of naphthalene-dicarboxylic acid; and
   the reaction is carried out by a continuous reaction method and water and methanol are continuously withdrawn.

18. The process according to claim 17 wherein the solvent comprises trimethyl trimellitate and at least one solvent selected from the group consisting of methyl benzoate, methyl toluate and dimethyl o-phthalate to form a mixed solvent;
   the amount of said at least one solvent selected from the group consisting of methyl benzoate, methyl toluate and dimethyl o-phthalate is at most one part by weight based on one part by weight of trimethyl trimellitate; and
   the mixed solvent is 1.5 to 7 parts by weight based on one part by weight of naphthalene-dicarboxylic acid.

19. The process according to claim 17 wherein the reaction is carried out in the presence of at least one catalyst selected from the group consisting of titanic acid ester, molybdophosphoric acid, molybdenum oxide, beryllium sulfate and bismuth sulfate.

20. The process according to claim 18 wherein the reaction is carried out in the presence of at least one catalyst selected from the group consisting of titanic acid ester, molybdophosphoric acid, molybdenum oxide, beryllium sulfate and bismuth sulfate.

21. The process according to claim 1 wherein the reaction is carried out at a temperature of about 270° to 280° C. and wherein the amount of solvent is about 2 to 3⅓ parts by weight based on one part by weight of naphthalene-dicarboxylic acid.

22. The process according to claim 21 wherein the solvent comprises trimethyl trimellitate and at least one solvent selected from the group consisting of methyl benzoate, methyl toluate and dimethyl o-phthalate to form a mixed solvent.

23. The process according to claim 21 wherein the reaction is carried out in the presence of molybdenum oxide as a catalyst.

* * * * *